US012678585B2

(12) United States Patent
Wang et al.

(10) Patent No.: US 12,678,585 B2
(45) Date of Patent: Jul. 14, 2026

(54) PERFUSION DEVICE, ANESTHETIC VAPORIZER, AND ANESTHETIC MACHINE

(71) Applicant: SHENZHEN MINDRAY BIO-MEDICAL ELECTRONICS CO., LTD., Shenzhen (CN)

(72) Inventors: Congquan Wang, Shenzhen (CN); Xuetao Wu, Shenzhen (CN); Peitao Chen, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 1050 days.

(21) Appl. No.: 17/854,165

(22) Filed: Jun. 30, 2022

(65) Prior Publication Data

US 2022/0331547 A1 Oct. 20, 2022

Related U.S. Application Data

(63) Continuation of application No. PCT/CN2019/130211, filed on Dec. 30, 2019.

(51) Int. Cl.
*A61M 16/18* (2006.01)
*A61M 16/20* (2006.01)

(52) U.S. Cl.
CPC ............ *A61M 16/18* (2013.01); *A61M 16/20* (2013.01)

(58) Field of Classification Search
CPC .. A61M 16/18–186; A61M 16/20–201; B65B 1/04; B65B 1/28; B65B 3/04; B65B 3/10–12; B65B 3/18
See application file for complete search history.

(56) References Cited

U.S. PATENT DOCUMENTS

| | | | |
|---|---|---|---|
| 5,505,236 A | 4/1996 | Grabenkort et al. | |
| 6,585,016 B1 | 7/2003 | Falligant et al. | |
| | (Continued) | | |

FOREIGN PATENT DOCUMENTS

| | | |
|---|---|---|
| CN | 102438688 A | 5/2012 |
| WO | 0027458 A1 | 5/2000 |
| WO | 2016059038 A1 | 4/2016 |

OTHER PUBLICATIONS

International Search Report issued in corresponding International Application No. PCT/CN2019/130211, mailed Oct. 10, 2020, 5 pages.

*Primary Examiner* — Rachel T Sippel
(74) *Attorney, Agent, or Firm* — PV IP PC; Wei Te Chung

(57) ABSTRACT

This disclosure provides a perfusion device, an anesthetic vaporizer, and an anesthetic machine. The anesthetic vaporizer includes a vaporizer body and the perfusion device. A feed port and a tank are provided in the vaporizer body. The perfusion device includes a mounting assembly, an ejector rod assembly, and a valve core assembly that is provided with a liquid inlet channel. The mounting assembly includes a mounting seat that is mounted on the feed port and provided with a hollow structure having an opening at both ends. The valve core assembly is movably mounted on one opening of the hollow structure, and the ejector rod assembly is movably mounted on the other opening of the hollow structure and forms a sealed structure with the mounting assembly. The ejector rod assembly may drive the valve core assembly to move toward the tank, and the liquid inlet channel communicates with the hollow structure.

17 Claims, 16 Drawing Sheets

(56)          References Cited

U.S. PATENT DOCUMENTS

| | | |
|---|---|---|
| 2006/0048842 A1 | 3/2006 | Bunke et al. |
| 2007/0199616 A1 | 8/2007 | Chotenovsky |
| 2013/0175235 A1* | 7/2013 | Elsayyid ............. A61M 16/183 |
| | | 215/316 |
| 2018/0243529 A1* | 8/2018 | Ito ....................... A61M 16/183 |
| 2020/0254210 A1* | 8/2020 | Bender, II ......... A61M 16/0891 |

* cited by examiner

111

1111b

1111

1111a

PERFUSION DEVICE, ANESTHETIC VAPORIZER, AND ANESTHETIC MACHINE

CROSS REFERENCE TO RELATED APPLICATIONS

This application is a continuation of Patent Cooperation Treaty Application No. PCT/CN2019/130211, filed on Dec. 30, 2019, which is hereby incorporated by reference in its entirety.

TECHNICAL FIELD

The disclosure relates to the technical field of medical devices, and more particularly to a perfusion device, an anesthetic vaporizer and an anesthetic machine.

BACKGROUND

An anesthetic vaporizer is an important part of an anesthetic machine, which vaporizes an anesthetic into a vaporized gas by utilizing changes in temperature and a heat source in surrounding environment, and then delivers the vaporized gas into breathing circuit by means of a carrier gas. Therefore, the anesthetic often needs to be added during use of the vaporizer.

At present, since the anesthetic may be continuously added into the anesthetic vaporizer even when a maximum liquid level is reached, a certain amount of the anesthetic remains at a feed port when an anesthetic bottle is removed. Because the anesthetic has characteristics of a low boiling point and volatility, the anesthetic exposed to the air may quickly volatilize into an anesthetic gas, which will harm medical care personnel in the surroundings.

SUMMARY

The disclosure provides a perfusion device, an anesthetic vaporizer and an anesthetic machine. The anesthetic vaporizer is capable of automatically stopping anesthetic feeding at the maximum liquid level, preventing any overflow and residual anesthetic during the anesthetic feeding and ensuring the safety of customers during the anesthetic feeding.

According to a first aspect of the disclosure, the disclosure provides an anesthetic vaporizer, including:

a vaporizer body provided with a feed port and a tank, the tank communicating with an outside via the feed port; and a perfusion device including a mounting assembly, an ejector rod assembly and a valve core assembly provided with a liquid inlet channel, the mounting assembly including a mounting seat mounted on the feed port, the mounting seat having a hollow structure with openings at its two ends, the valve core assembly being movably mounted on an opening at one end of the hollow structure facing the tank, the ejector rod assembly being movably mounted on an opening at the other end of the hollow structure and forming a sealed structure with the mounting assembly, the ejector rod assembly driving the valve core assembly to move toward the tank under an external force, and the liquid inlet channel communicating with the hollow structure.

In the anesthetic vaporizer of the disclosure, the hollow structure includes an inlet section and an outlet section, the diameter of the outlet section being smaller than that of the inlet section, the ejector rod assembly being mounted in the inlet section, and the valve core assembly being mounted in the outlet section.

In the anesthetic vaporizer of the disclosure, the ejector rod assembly includes an ejector rod and an elastic member, one end of the elastic member abutting against the ejector rod, and the other end of the elastic member abutting against an end of the inlet section close to the outlet section.

In the anesthetic vaporizer of the disclosure, an end of the ejector rod facing the valve core assembly is provided with a connection end, the diameter of the connection end is smaller than that of the outlet section, and the valve core assembly is connected to the connection end.

In the anesthetic vaporizer of the disclosure, the valve core assembly is provided with a connection portion, and the valve core assembly is connected to the connection end by means of the connection portion.

In the anesthetic vaporizer of the disclosure, at least one valve core through hole which communicates with the liquid inlet channel is provided between the connection portion and the valve core assembly.

In the anesthetic vaporizer of the disclosure, the mounting assembly further includes a liquid injection seat that connects to a mouth of an anesthetic bottle, the inlet section is provided with a liquid injection seat mounting recess, and the liquid injection seat is mounted on the liquid injection seat mounting recess so as to constrain the ejector rod assembly within the hollow structure.

In the anesthetic vaporizer of the disclosure, the liquid injection seat is provided with an ejection portion, and when the mouth of the anesthetic bottle is connected to the liquid injection seat, a sealing device mounted in the mouth of the anesthetic bottle is ejected by the ejection portion.

In the anesthetic vaporizer of the disclosure, the ejection portion is provided with a liquid inlet hole running through two ends along its axis direction, and the liquid inlet hole corresponds in position to the mouth of the anesthetic bottle connected to the liquid injection seat.

In the anesthetic vaporizer of the disclosure, at least one penetrating hole is provided between the ejection portion and the liquid injection seat, the ejector rod is provided with an extension which penetrates the penetrating hole, and when the anesthetic bottle is placed on the liquid injection seat, the anesthetic bottle is capable of driving the ejector rod away from the liquid injection seat by means of the extension.

In the anesthetic vaporizer of the disclosure, a length of the extension extending from the liquid injection seat is less than a length of the ejection portion extending from the liquid injection seat.

In the anesthetic vaporizer of the disclosure, the ejector rod assembly further includes a first seal disposed between the ejector rod and the liquid injection seat.

In the anesthetic vaporizer of the disclosure, a second seal is provided between the liquid injection seat and the mounting seat, and the liquid injection seat is provided with a seal mounting groove in which the second seal is mounted.

In the anesthetic vaporizer of the disclosure, a third seal is provided between the mounting seat and the feed port, a seal groove is provided along a periphery of the mounting seat, and the third seal is mounted in the seal groove.

In the anesthetic vaporizer of the disclosure, a distance between an end of the valve core assembly facing the tank and the tank is equal to a preset distance.

According to a second aspect of the disclosure, the disclosure further provides an anesthetic machine, including:

a main body provided with a vaporizer connection seat and a gas passage interface communicating with a breathing circuit; and the anesthetic vaporizer described above, the anesthetic vaporizer being mounted on the vaporizer connection seat, and a gas supply and delivery system being connected to the anesthetic vaporizer such that the anesthetic vaporizer is capable of providing respiratory support to a patient through the breathing circuit.

According to a third aspect of the disclosure, the disclosure further provides a perfusion device for use in an anesthetic vaporizer having a feed port, including:

a mounting assembly including a mounting seat having a hollow structure with openings at its two ends;

an ejector rod assembly movably mounted on an opening at one end of the hollow structure; and a valve core assembly movably mounted on an opening at the other end of the hollow structure, the valve core assembly being connected to the ejector rod assembly such that the ejector rod assembly is capable of driving the valve core assembly to move in an axial direction of the hollow structure. The valve core assembly includes a liquid inlet channel; when the ejector rod assembly drives the valve core assembly to move away from the end of the hollow structure mounted with the valve core assembly, the liquid inlet channel becomes communicating communicates with the hollow structure.

The technical solutions provided in the embodiments of the present application may include the following beneficial effects: a perfusion device, an anesthetic vaporizer and an anesthetic machine are designed in the disclosure, since each of the ejector rod assembly and the valve core assembly may be movably mounted in the hollow structure, when the ejector rod assembly is driven by an external force, the valve core assembly may be driven to move toward the tank, such that the anesthetic in the anesthetic bottle can enter the tank through the hollow structure and the liquid inlet channel, and when the anesthetic in the tank covers the liquid inlet channel, an exhaust passage between the tank and the anesthetic bottle is cut off, and anesthetic feeding to the tank is automatically stopped, which prevents any overflow and residual anesthetic during the anesthetic feeding and ensures the safety of the anesthetic feeding for the operation personnel.

It should be understood that the above general description and the following detailed description are only exemplary and explanatory, and cannot limit the present application.

BRIEF DESCRIPTION OF THE DRAWINGS

In order to more clearly describe the technical solutions in embodiments of the disclosure, the drawings required for describing the embodiments will be briefly described below. Apparently, the drawings in the following description show some of the embodiments of the disclosure, and persons of ordinary skill in the art may still derive other drawings from these drawings without creative efforts.

FIG. 13 is a schematic structural view of the valve core assembly in FIG. 1;

LIST OF REFERENCE NUMERALS

Figure 1:
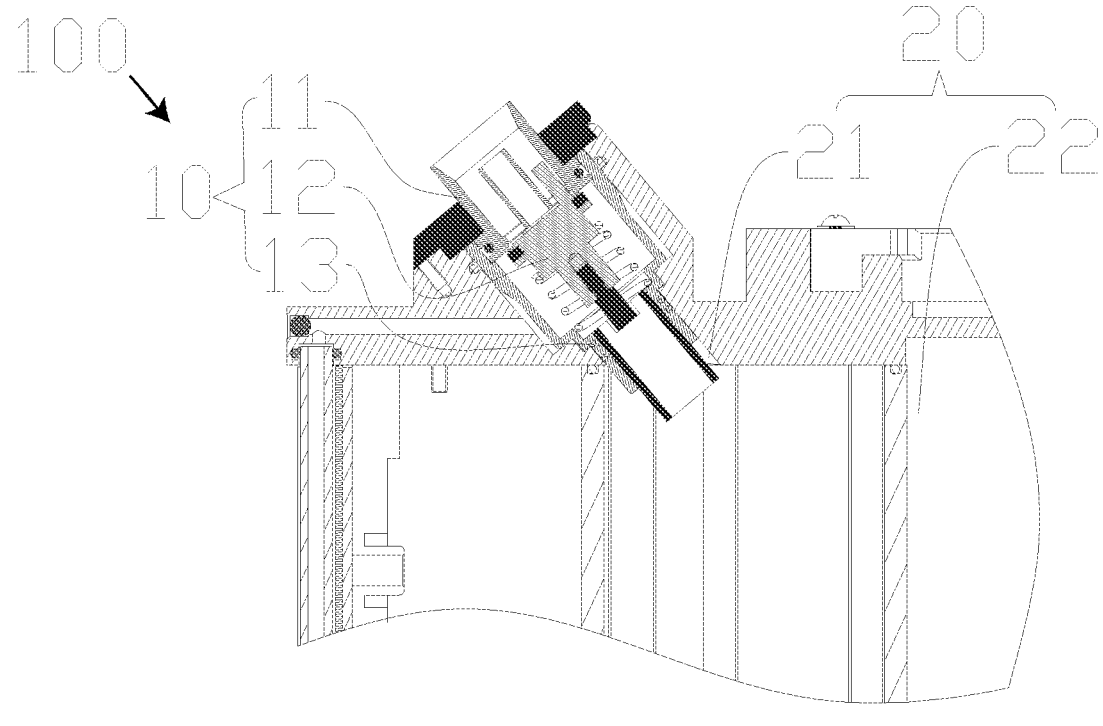
FIG. 1 is a partial cross-sectional view of an anesthetic vaporizer according to an embodiment of the disclosure.
Figure 2:
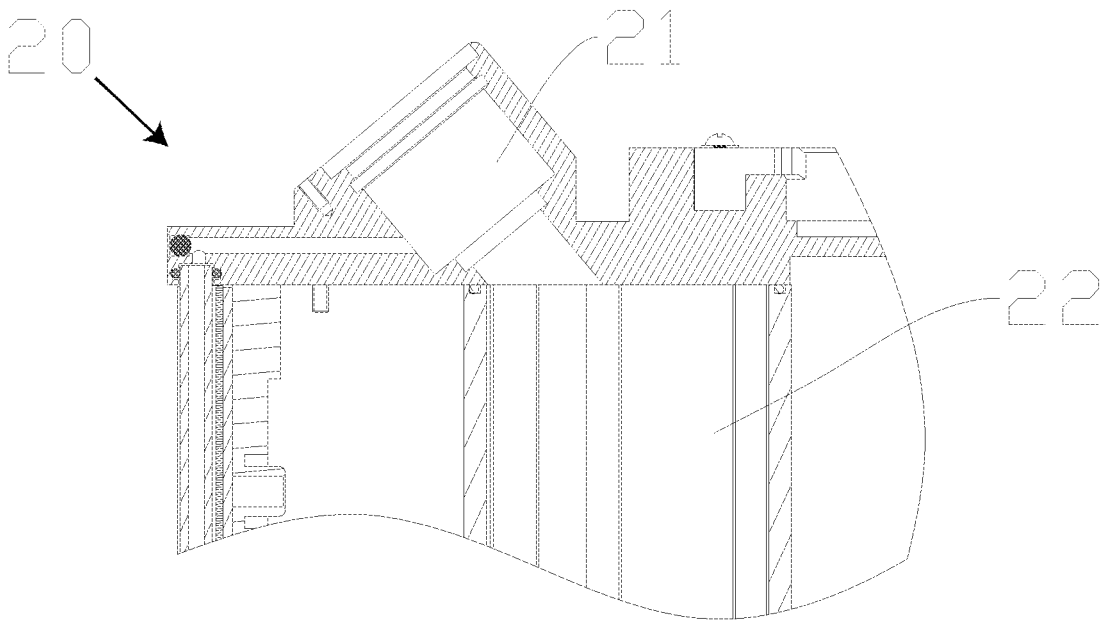
FIG. 2 is a partial cross-sectional view of a vaporizer body in FIG. 1.
Figure 3:
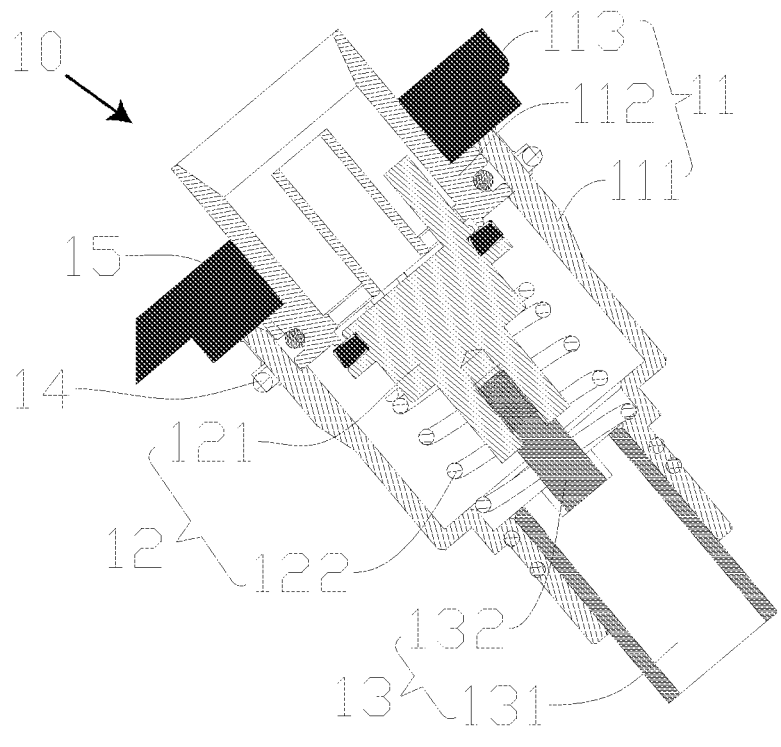
FIG. 3 is a schematic cross-sectional view of a perfusion device in FIG. 1.
Figure 4:
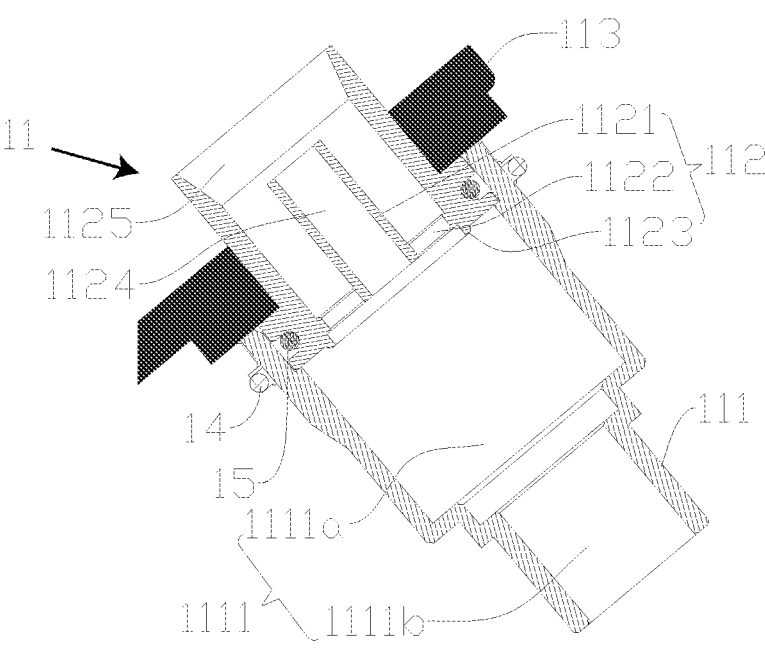
FIG. 4 is a schematic cross-sectional view of a mounting assembly in FIG. 1.
Figure 5:
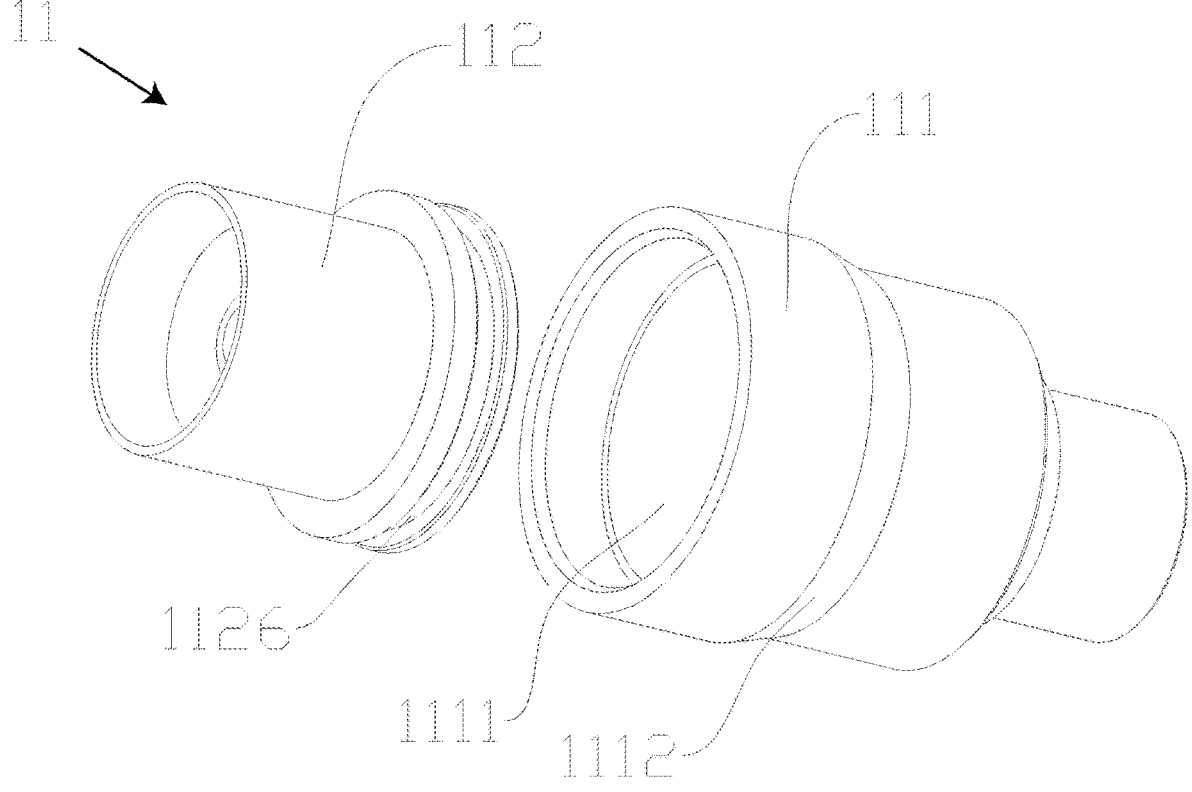
FIG. 5 is a partial cross-sectional view of a mounting assembly in FIG. 1.
Figure 6:
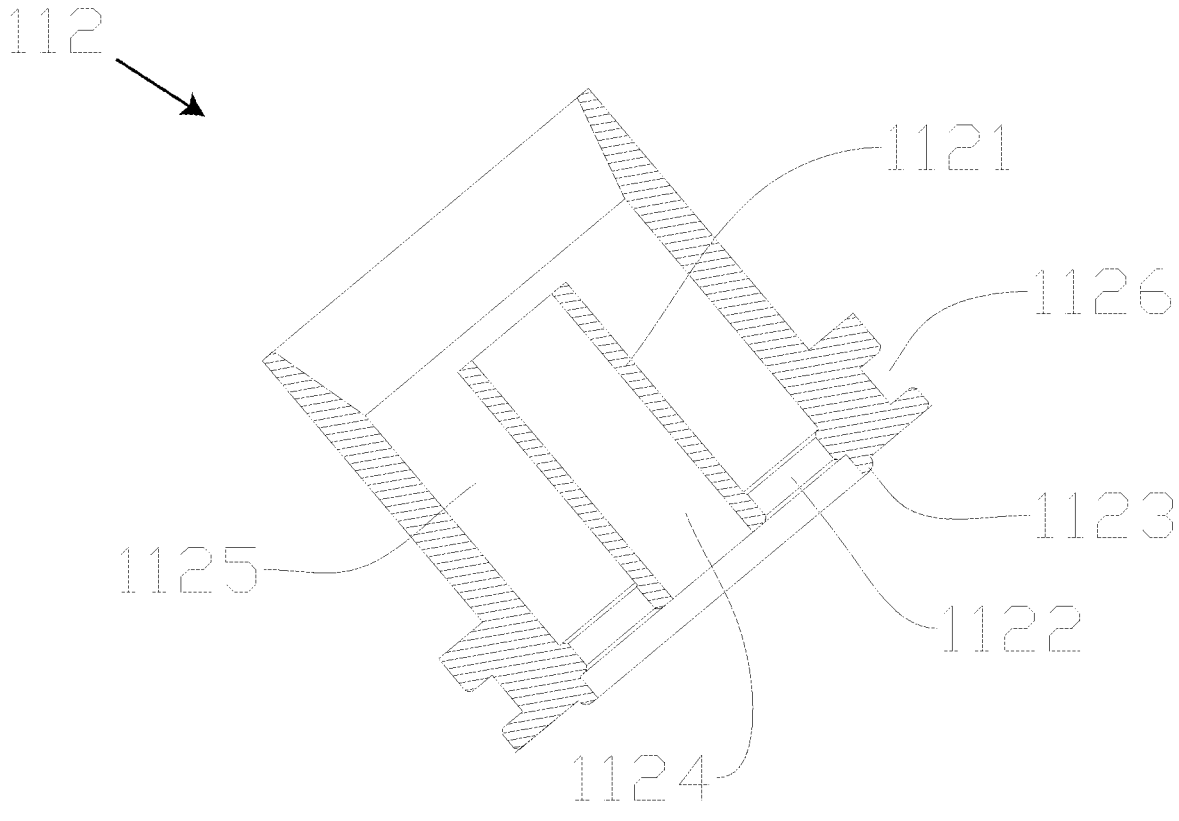
FIG. 6 is a schematic cross-sectional view of a liquid injection seat in FIG. 1.
Figure 7:
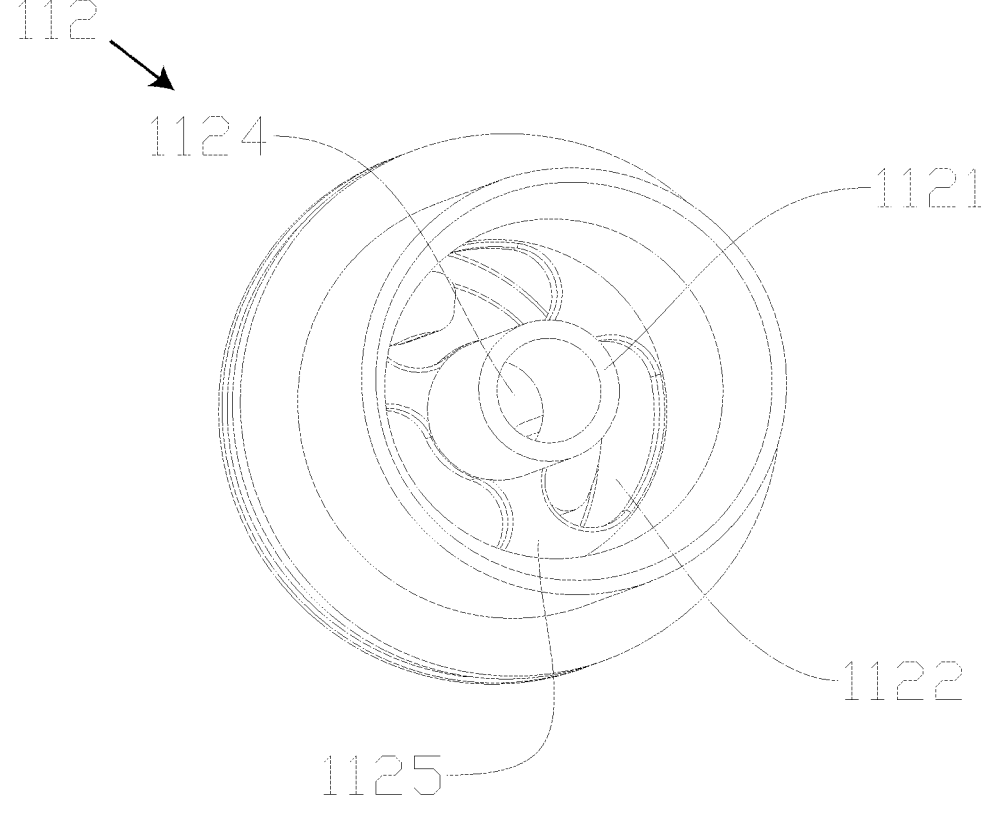
FIG. 7 is a schematic structural view of a liquid injection seat in FIG. 1.
Figure 8:
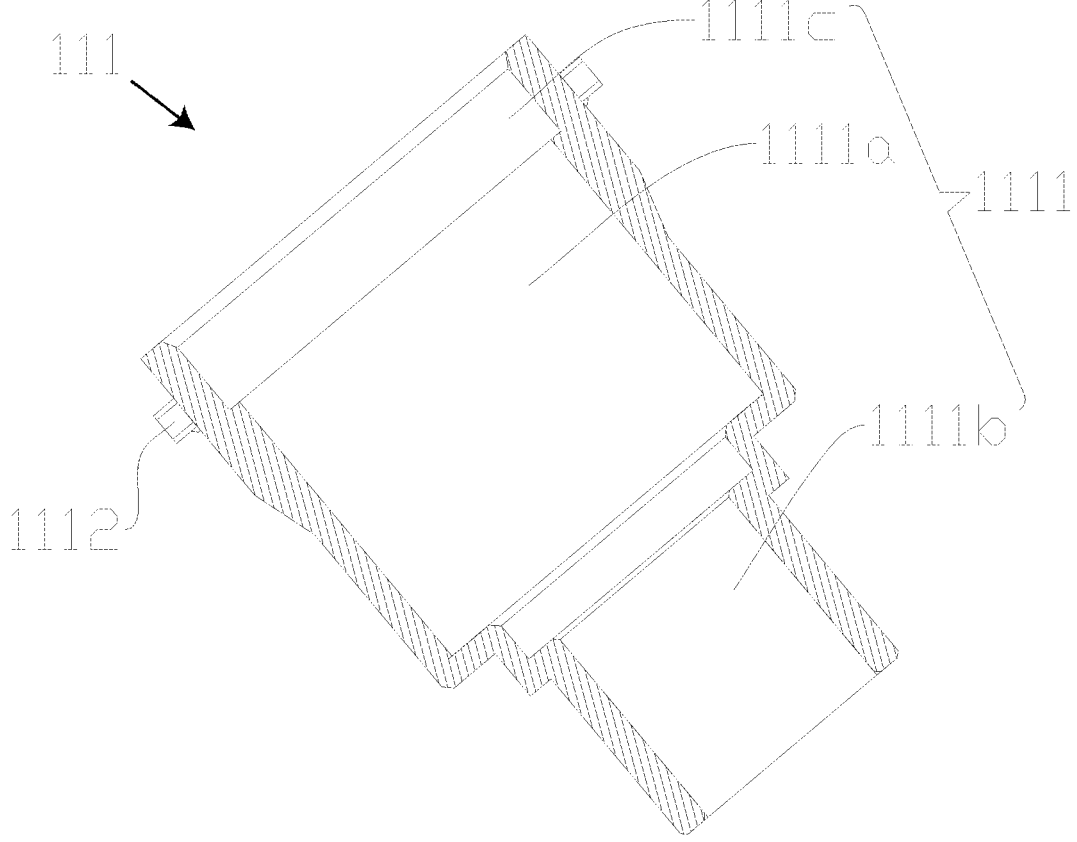
FIG. 8 is a schematic cross-sectional view of a mounting seat in FIG. 1.
Figure 9:
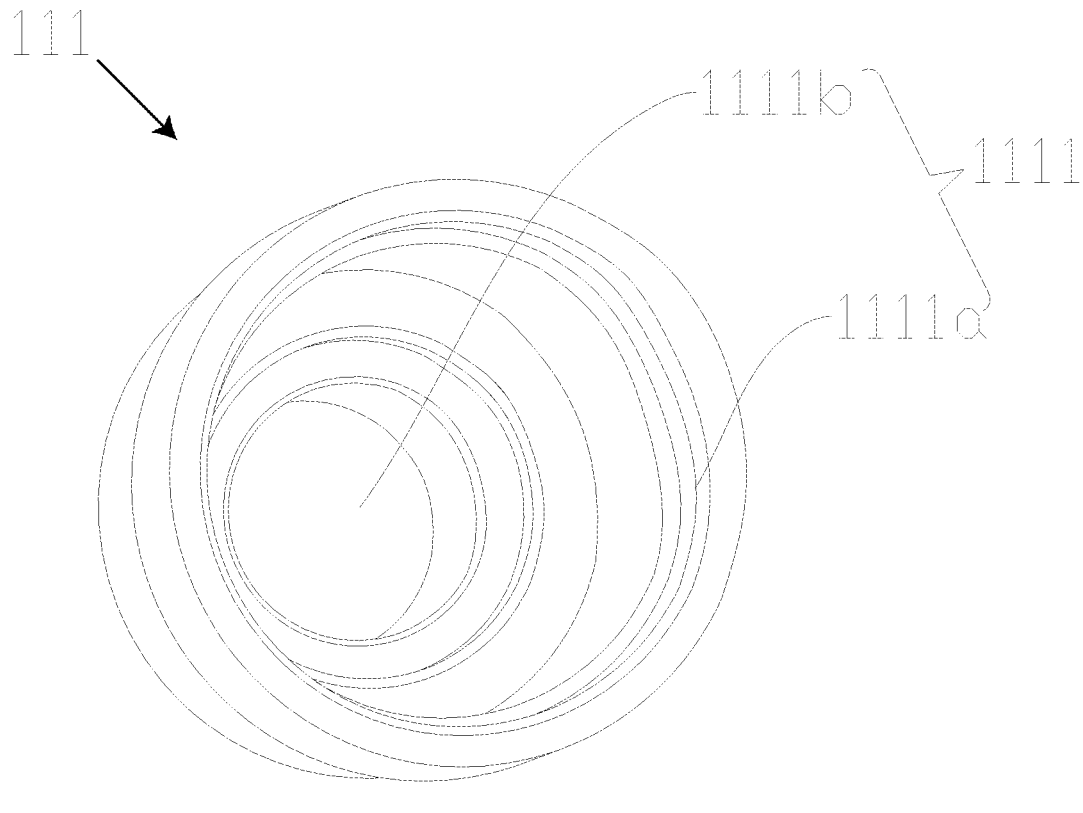
FIG. 9 is a schematic structural view of a mounting seat in FIG. 1.
Figure 10:
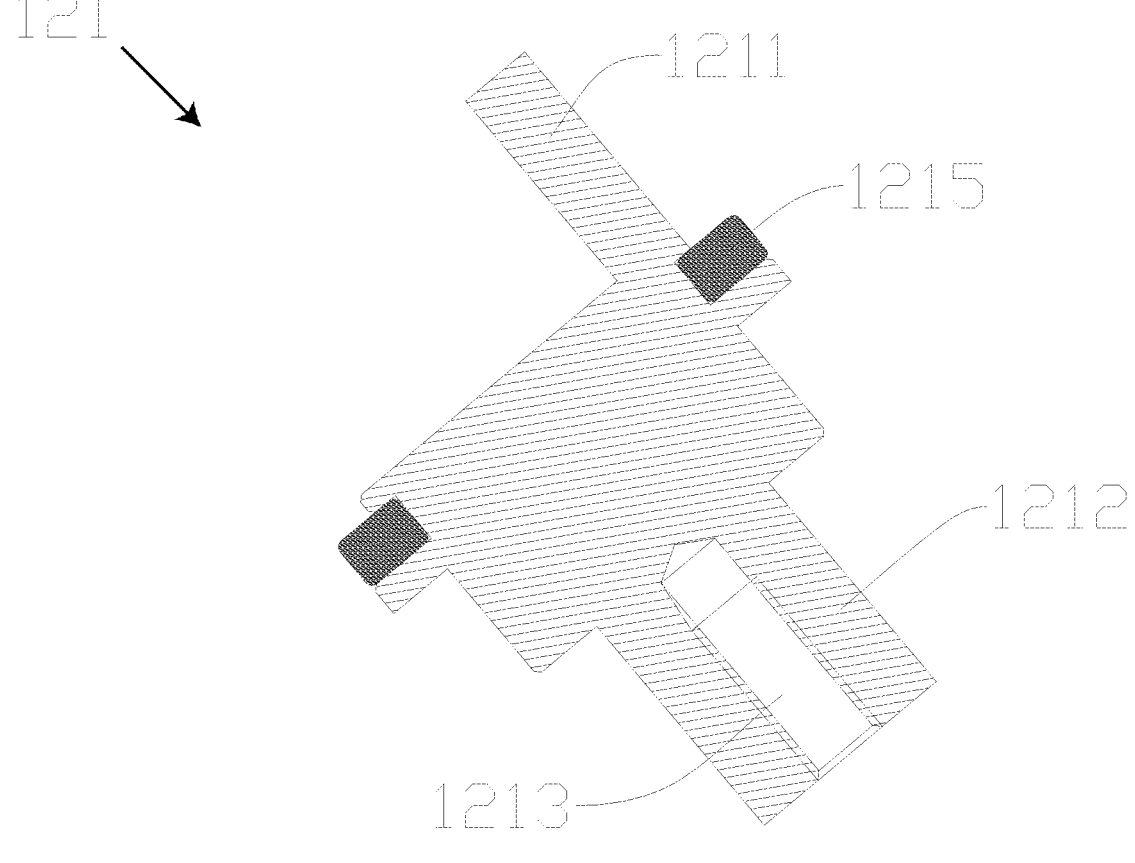
FIG. 10 is a partial cross-sectional view of an ejector rod assembly in FIG. 1.
Figure 11:
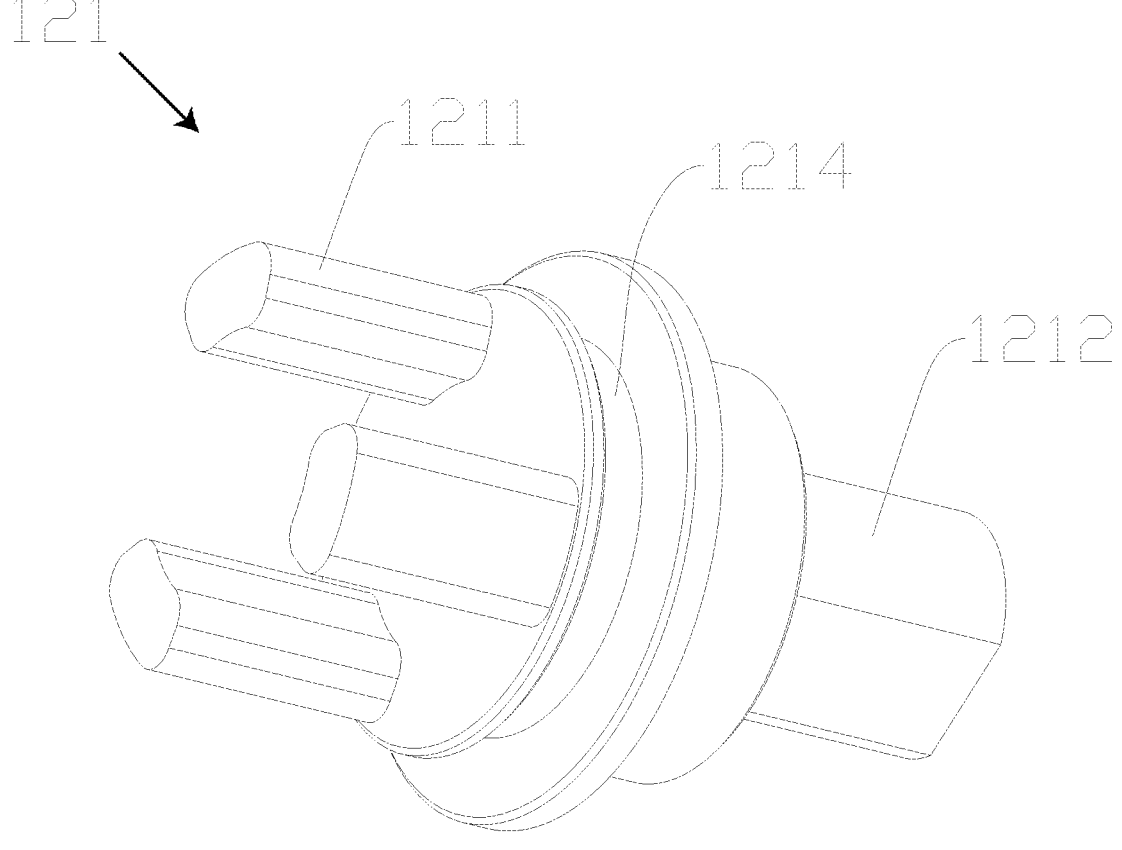
FIG. 11 is a partial schematic view of an ejector rod assembly in FIG. 1.
Figure 12:
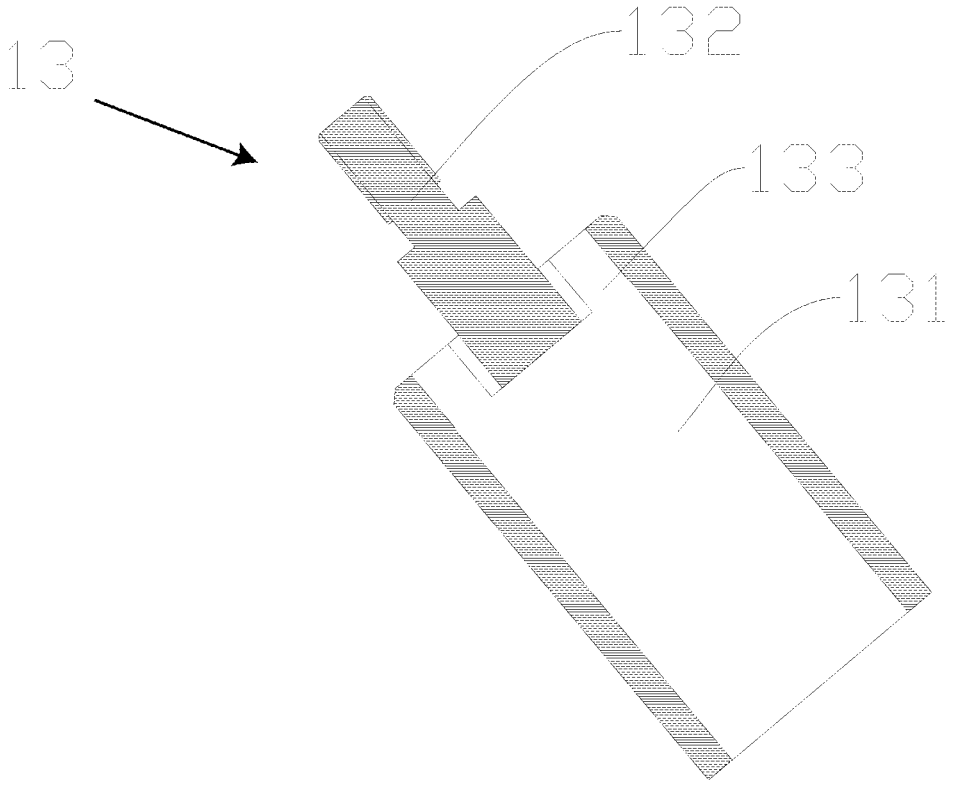
FIG. 12 is a schematic cross-sectional view of a valve core assembly in FIG. 1.
Figure 13:
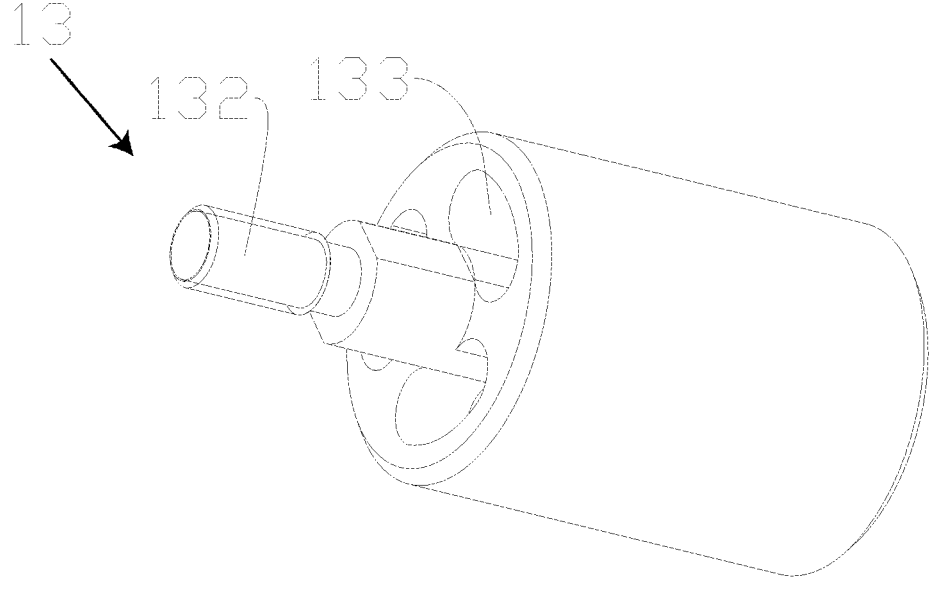
FIG. 13 is a schematic structural view of a valve core assembly in FIG. 1.

100. Anesthetic vaporizer;

10. Perfusion device; 11. Mounting assembly; 111. Mounting seat; 1111. Hollow structure; 1111*a*. Inlet section; 1111*b*. Outlet section; 1111*c*. Liquid injection seat mounting recess; 1112. Seal groove; 112. Liquid injection seat; 1121. Ejection portion; 1122. Penetrating hole; 1123. Liquid injection seat protrusion; 1124. Liquid inlet hole; 1125. Liquid injection seat groove; 1126. Seal mounting groove; 113. Fixing seat; 12. Ejector rod assembly; 121. Ejector rod; 1211. Extension; 1212. Connection end; 1213. Connection end screw hole; 1214. Ejector rod groove; 1215. Sealing gasket; 122. Elastic member; 13. Valve core assembly; 14. Third seal; 15. Second seal; 131. Liquid inlet channel; 132. Connection portion; 133. Valve core through hole; 20. Vaporizer body; 22. Tank; 21. Feed port;

200. Anesthetic bottle; 201. Sealing device; 202. Seal; 2011. Anesthetic outlet; 203. Feed adapter; and 2031. Sealing assembly.

DETAILED DESCRIPTION

The technical solutions of the embodiments of the disclosure will be described below clearly and comprehensively in conjunction with accompanying drawings of the embodiments of the disclosure. Apparently, the embodiments described are some of, rather than all of, the embodiments of the disclosure. All other embodiments obtained by persons of ordinary skill in the art based on the embodiments of the disclosure without creative efforts shall fall within the scope of protection of the disclosure.

In the description of the disclosure, it should be understood that the orientation or position relationship indicated by the terms "central", "lengthwise", "transverse", "length", "width", "thickness", "upper", "lower", "front", "rear", "left", "right", "vertical", "horizontal", "top", "bottom", "inner", "outer", "clockwise", "counterclockwise", etc. are based on the orientation or position relationship shown in the accompanying drawings and are intended to facilitate the description of the disclosure and simplify the description only, rather than indicating or implying that the apparatus or element referred to must have a particular orientation or be constructed and operated in a particular orientation, and therefore cannot be understood as limiting the disclosure. In addition, the terms "first" and "second" are used for descriptive purposes only, and cannot be construed as indicating or implying relative importance or implicitly indicating the number of technical features indicated. Thus, the features defined with "first" and "second" may explicitly or implicitly include one or more of the features. In the description of the disclosure, the meaning of "a plurality of" is two or more, unless specifically and specifically limited otherwise.

Some embodiments of the disclosure will be further described in detail below with reference to the drawings. In the case of no conflict, the embodiments and the features thereof described below can be combined with each other.

An anesthetic vaporizer in the disclosure relates to the technical field of medical devices and is applied in an anesthetic machine. The anesthetic machine is an auxiliary device for a surgery and is configured to anesthetize a patient with an anesthetic during surgery so as to make the patient lose consciousness and sensation, thereby alleviating the pain of the patient during surgery and facilitating the smooth progress of a surgery.

Specifically, the anesthetic machine includes a main body, a gas supply and delivery system, a ventilator configured to mix an anesthetic gas and an oxygen, and an anesthetic vaporizer configured to vaporize an anesthetic, where the gas supply and delivery system is connected to the anesthetic vaporizer, and the anesthetic vaporizer is connected to the ventilator by means of a breathing circuit such that the patient may breathe by virtue of the ventilator, thereby enabling the anesthetic machine to anesthetize the patient.

However, anesthetic feeding is necessary during use of the anesthetic vaporizer. Since the anesthetic feeding may continue even when a maximum liquid level of a tank is reached for the anesthetic vaporizer. Thus, a certain amount of anesthetic remains at a feed port of the anesthetic vaporizer when an anesthetic bottle is pulled out. Due to the fact that the anesthetic has characteristics of a low boiling point and volatility, the anesthetic exposed to the air may quickly volatilize into an anesthetic gas, which will harm medical care personnel in the surroundings.

As shown in FIGS. 1 to 13, according to a first aspect of the disclosure, the disclosure provides an anesthetic vaporizer 100. The anesthetic vaporizer 100 includes a perfusion device 10 and a vaporizer body 20, where the vaporizer body 20 is provided with a feed port 21 and a tank 22, and the tank 22 communicates with an outside via a feed port 21. The perfusion device 10 includes a mounting assembly 11, an ejector rod assembly 12, and a valve core assembly 13 that is provided with a liquid inlet channel 131. In this embodiment, the mounting assembly 11 includes a mounting seat 111 that is mounted on the feed port 21 and is provided with a hollow structure 1111 having openings at its two ends, where the valve core assembly 13 may be movably mounted on an opening at one end of the hollow structure 1111 facing the tank 22, and the ejector rod assembly 12 may be movably mounted on an opening at the other end of the hollow structure 1111 and forms a sealed structure with the mounting assembly 11. When the ejector rod assembly 12 is driven by an external force to drive the valve core assembly 13 to move toward the tank 22, the liquid inlet channel 131 communicates with the hollow structure 1111 such that an anesthetic in an anesthetic bottle can enter the tank 22 through the hollow structure 1111 and the liquid inlet channel 131.

Specifically, when the anesthetic is added from the anesthetic bottle to the tank 22 by means of the perfusion device 10, the anesthetic bottle abuts against the ejector rod assembly 12 and drives the ejector rod assembly 12 to move toward the tank 22, which may not only release the sealed structure formed between the ejector rod assembly 12 and the mounting assembly 11, but also drive the valve core assembly 13 to move toward the tank 22, such that the liquid inlet channel 131 communicates with the hollow structure 1111 to allow the anesthetic in the anesthetic bottle to enter the tank 22 through the hollow structure 1111 and the liquid inlet channel 131.

During anesthetic feeding of the anesthetic vaporizer 100, the anesthetic in the anesthetic bottle enters the tank 22 through the hollow structure 1111 and the liquid inlet channel 131, and a gas in the tank 22 enters the anesthetic bottle through the liquid inlet channel 131 and the hollow structure 1111 to form a circulation loop. After the anesthetic in the tank 22 covers the opening at the end of the liquid inlet channel 131 facing the tank 22, an exhaust passage between the tank 22 and the anesthetic bottle is cut off, and the anesthetic feeding is automatically stopped.

When the anesthetic bottle is moved away from the perfusion device 10, the ejector rod assembly 12 returns to its original position and drives the valve core assembly 13 to move in an opposite direction of the tank 22, the opening at the end of the liquid inlet channel 131 facing the tank 22 is re-opened, and the residual anesthetic in the liquid inlet channel 131 re-enters into the tank 22 until the anesthetic in the anesthetic bottle does not continue flowing into the tank 22 after the ejector rod assembly 12 and the mounting assembly 11 forms the sealed structure. In addition, the anesthetic bottle itself also has a sealing device which is configured for sealing before the ejector rod assembly 12 and the mounting assembly 11 forms the sealed structure, so as to ensure that no anesthetic remains in the hollow structure 1111 when the anesthetic bottle is pulled out from the perfusion device 10.

With the above-described technical solution, since the valve core assembly 13 may be movably mounted in the hollow structure 1111 by means of the ejector rod assembly 12, the ejector rod assembly and the mounting assembly 11 forms the sealed structure when the ejector rod assembly 12 is not driven by an external force, and the valve core assembly 13 is driven to move toward the tank 22 when the ejector rod assembly 12 is driven by an external force such that the liquid inlet channel 131 communicates with the hollow structure 1111 to allow the anesthetic in the anesthetic bottle to enter into the tank 22 through the hollow structure 1111 and the liquid inlet channel 131. After the anesthetic in the tank 22 covers the opening at the end of the liquid inlet channel 131 facing the tank 22, the exhaust passage between the tank 22 and the anesthetic bottle is cut off and the anesthetic feeding is automatically stopped, which prevents any overflow and residual anesthetic during anesthetic feeding in the anesthetic vaporizer 100, thereby ensuring the health of anesthetic feeding personnel.

In an alternative embodiment, the hollow structure 1111 includes an inlet section 1111*a* and an outlet section 1111*b*, and the diameter of the outlet section 1111*b* is smaller than that of the inlet section 1111*a*, where the ejector rod assembly 12 is mounted in the inlet section 1111*a* and the valve core assembly 13 is mounted in the outlet section 1111*b*, which not only facilitates mounting the ejector rod assembly 12 and the valve core assembly 13 in the hollow structure 1111, but also allows the valve core assembly 13 to move along the outlet section 1111*b* in an axial direction of the hollow structure 1111. It is thus ensured that the anesthetic in the anesthetic bottle can enter the tank 22 through the hollow structure 1111 and the liquid inlet channel 131, and after the anesthetic in the tank 22 covers the opening at the end of the liquid inlet channel 131 facing the tank 22, the anesthetic vaporizer 100 can automatically stop the anesthetic feeding, which prevents overflow and residual anesthetic in the anesthetic vaporizer 100 during the anesthetic feeding, thereby ensuring the health of the anesthetic feeding personnel.

In an alternative embodiment, the ejector rod assembly 12 includes an ejector rod 121 and an elastic member 122, where one end of the elastic member 122 abuts against the ejector rod 121, and the other end of the elastic member 122 abuts against one end of the inlet section 1111*a* close to the outlet section 1111*b*.

Specifically, the ejector rod assembly 12 further includes a first seal disposed between the ejector rod 121 and the mounting assembly 11. In this embodiment, a sealing gasket 1215 is disposed at one end of the ejector rod 121 away from the valve core assembly 13, the sealing gasket 1215 always abuts against the mounting assembly 11 under the action of the elastic member 122 and forms the sealed structure with the mounting assembly 11.

When the anesthetic is added from the anesthetic bottle to the tank 22 by means of the perfusion device 10, the ejector rod 121 is driven by the anesthetic bottle such that the elastic member 122 deforms, and the anesthetic bottle continues driving the ejector rod 121 to break the abutting relationship between the sealing gasket 1215 and the mounting assembly 11, and the valve core assembly 13 moves toward the tank 22 under the drive of the ejector rod 121. When the anesthetic bottle is pulled out from the perfusion device 10, the elastic member 122 returns to its original state. While the ejector rod 121 drives the valve core assembly 13 to return to its original position under the return action of the elastic member 122, the sealing gasket 1215 abuts against the mounting assembly 11 again to form the sealed structure with the mounting assembly 11, preventing volatilization of the anesthetic in the tank 22 to outside and impair on the health of the anesthetic feeding personnel.

In an alternative embodiment, the end of the ejector rod 121 facing the valve core assembly 13 is provided with a connection end 1212, and the connection end 1212 has a diameter smaller than the outlet section 1111*b* such that the connection end 1212 can freely move within the outlet section 1111*b*. In this embodiment, the connection end 1212 is provided with a connection end screw hole 1213, the valve core assembly 13 is provided with a valve core stud, the valve core assembly 13 is fixed to the connection end 1212 by means of a fitting connection between the valve core stud and the connection end screw hole 1213, and the elastic member 122 is sleeved on the connection end 1212, such that the ejector rod 121 can drive the valve core assembly 13 to move within the outlet section 1111*b*.

In an alternative embodiment, a seal is formed between the valve core assembly 13 and the outlet section 1111*b* by a seal ring, ensuring that the gas in the tank 22 can only be exhausted through the liquid inlet channel 131 during anesthetic feeding in the anesthetic vaporizer 100. After the anesthetic in the tank 22 covers the opening at the end of the liquid inlet channel 131 facing the tank 22, the exhaust passage between the tank 22 and the anesthetic bottle is cut off, and the anesthetic feeding is automatically stopped.

It should be noted that the valve core assembly 13 may be integrally formed with the ejector rod 121, or a seal may also be formed between the valve core assembly 13 and the outlet section 1111*b* by other sealing means, or the valve core assembly and the outlet section may also be in clearance fit with a little fit tolerance, which is not limited in the disclosure.

In an alternative embodiment, the valve core assembly 13 is provided with a connection portion 132, the valve core stud is disposed on the connection portion 132, and the connection portion 132 has a diameter that is much smaller than that of the valve core assembly 13, which facilitates providing some pores between the connection portion 132 and the valve core assembly 13. When the valve core assembly 13 is connected to the connection end 1212 by means of the connection portion 132, the anesthetic in the anesthetic bottle can enter the liquid inlet channel 131 through the pores between the connection portion 132 and the valve core assembly 13, and meanwhile, the gas in the tank 22 can be exhausted through the liquid inlet channel 131 via the pores between the connection portion 132 and the valve core assembly 13.

In an alternative embodiment, at least one valve core through hole 133 is provided between the connection portion 132 and the valve core assembly 13, where the valve core through hole 133 communicates with the liquid inlet channel 131 such that the anesthetic outside the anesthetic vaporizer 100 can enter the tank 22 via the valve core through hole 133 through the liquid inlet channel 131, and meanwhile, the gas in the tank 22 can be exhausted outside through the liquid inlet channel 131 via the valve core through hole 133.

In this embodiment, three valve core through holes 133 are provided, and the three valve core through holes 133 are arranged in an annular array between an outer side of the connection portion 132 and an inner side of the liquid inlet channel 131 in a radial direction, such that not only the connection stability of the connection portion 132 can be ensured, but also it is ensured that the anesthetic can enter the liquid inlet channel 131 through one of the valve core through holes 133, and the gas in the tank 22 can be exhausted through other valve core through holes 133.

In an alternative embodiment, the mounting assembly 11 further includes a liquid injection seat 112 that connects to a mouth of the anesthetic bottle, where the inlet section 1111*a* is provided with a liquid injection seat mounting recess 1111*c*, and the liquid injection seat 112 is mounted on the liquid injection seat mounting recess 1111*c* so as to constrain the ejector rod assembly 12 within the hollow structure 1111.

Specifically, after the valve core assembly 13 is connected to the ejector rod assembly 12, the ejector rod assembly 12 and the valve core assembly 13 are mounted in the hollow structure 1111, and then the liquid injection seat 112 is mounted on the liquid injection seat mounting recess 1111*c*, such that the valve core assembly 13 can only move within a segment of the inlet section 1111*a* facing away from the liquid injection seat 112, namely, the valve core assembly 13 moves within a range between the liquid injection seat 112 and the outlet section 1111*b*, thereby constraining the ejector rod assembly 12 and the valve core assembly 13 within the hollow structure 1111. The structure is simple, the mounting and dismounting is convenient, and the replacement and maintenance of the perfusion device 10 is easy.

In an alternative embodiment, the liquid injection seat 112 is provided with an ejection portion 1121, a sealing device mounted in the mouth of the anesthetic bottle is ejected by the ejection portion 1121 when the mouth of the anesthetic bottle is connected to the liquid injection seat 112, such that the anesthetic can enter the liquid injection seat 112 through the mouth of the anesthetic bottle and flow into the liquid inlet channel 131 and then the tank 22 through the hollow structure 1111 by means of the liquid injection seat 112.

Specifically, a liquid injection seat channel 1125 is formed in the liquid injection seat 112, and the ejection portion 1121 is disposed in the middle of the liquid injection seat channel 1125, where a diameter of the liquid injection seat channel 1125 is adapted to an outer diameter of the mouth of the anesthetic bottle such that the mouth of the anesthetic bottle can be inserted into the liquid injection seat channel 1125. In this embodiment, the anesthetic bottle is provided with a seal at a position close to the mouth of the anesthetic bottle. When the mouth of the anesthetic bottle is inserted into the liquid injection seat channel 1125, an outer side of the seal abuts against an inner wall of the liquid injection seat channel 1125, so as to isolate the liquid injection seat channel 1125 from the outside at the mouth of the anesthetic bottle, and to prevent volatilization of the anesthetic on the mouth of the anesthetic bottle to the outside from a gap between the outer side of the mouth of the anesthetic bottle and the diameter of the liquid injection seat channel 1125 during the anesthetic feeding, which will prevent impairing the health of the anesthetic feeding personnel.

In an alternative embodiment, the ejection portion 1121 is provided with a liquid inlet hole 1124 running through its two axial ends, where the position of the liquid inlet hole 1124 corresponds to the mouth of the anesthetic bottle connected to the liquid injection seat, such that the anesthetic can enter the liquid inlet hole 1124 through the mouth of the anesthetic bottle, and then enter the tank 22 successively through the liquid inlet hole 1124, the hollow structure 1111, the valve core through hole 133 and the liquid inlet channel 131.

Specifically, the sealing device in the mouth of the anesthetic bottle is provided with an anesthetic outlet. When the ejection portion 1121 ejects the sealing device, the anesthetic in the anesthetic bottle can flow into the liquid inlet hole 1124 through the anesthetic outlet, and then enters the tank 22 through the liquid inlet channel 131. When the mouth of the anesthetic bottle is separated from the liquid injection seat channel 1125, the sealing device returns to its original position to prevent volatilization of the anesthetic in the anesthetic bottle to outside through the anesthetic outlet, to prevent impairing the health of the anesthetic feeding personnel.

In an alternative embodiment, at least one penetrating hole 1122 is provided between the ejection portion 1121 and the liquid injection seat 112, where the ejector rod 121 is provided with an extension 1211, and the extension 1211 penetrates the penetrating hole 1122. When the anesthetic bottle is placed on the liquid injection seat 112, the anesthetic bottle can drive the ejector rod 121 away from the liquid injection seat 112 by means of the extension 1211.

Specifically, three extensions 1211 are provided, and the number of the penetrating holes 1122 corresponds to the number of the extensions 1211. In this embodiment, the three extensions 1211 centered on a central axis of the ejector rod 121 are arranged at an end of the ejector rod 121 away from the connection end 1212, where an end of the ejector rod 121 close to the extensions 1211 is provided with an ejector groove 1214, and a liquid injection seat protrusion 1123 is provided at a position, opposite to the ejector groove 1214, on the liquid injection seat 112. After the sealing gasket 1215 is mounted in the ejector groove 1214, the sealing gasket 1215 can abut against the liquid injection seat protrusion 1123 to ensure sealing between the ejector rod 121 and the liquid injection seat 112.

In an alternative embodiment, the length of the extension 1211 extending from the liquid injection seat 112 is less than the length of the ejection portion 1121 extending from the liquid injection seat 112, such that when the mouth of the anesthetic bottle is inserted into the liquid injection seat channel 1125, the anesthetic bottle drives the ejector rod 121 by means of the extension 1211 to move the valve core assembly 13 toward the tank 22 after the ejection portion 1121 can drive the sealing device at a distance away from the liquid injection seat 112. Generally, an unsealing length required for the sealing device is greater than a sealing distance of the ejector rod 121 relative to the liquid injection seat 112. Therefore, with the above technical solution, it may be ensured that the anesthetic bottle is opened by the ejection portion 1121 while the liquid inlet channel 131 communicates with the hollow structure 1111, such that the anesthetic in the anesthetic bottle is allowed to enter the tank 22 from the mouth of the anesthetic bottle through the hollow structure 1111 and the liquid inlet channel 131.

In an alternative embodiment, a second seal 15 is provided between the liquid injection seat 112 and the mounting seat 111, where the liquid injection seat 112 is provided with a seal mounting groove 1126, the second seal 15 is mounted on the seal mounting groove 1126, and an outer side of the second seal 15 abuts against an inner wall of the mounting seat 111, ensuring that the gas in the tank 22 can only be exhausted to the interior of the anesthetic bottle through the liquid inlet channel 131, and also preventing volatilization of the anesthetic volatilize to outside through the gap between the liquid injection seat 112 and the mounting seat 111 and the impair on the health of the anesthetic feeding personnel.

In an alternative embodiment, a third seal 14 is provided between the mounting seat 111 and the feed port 21, a seal groove 1112 is provided along the periphery of the mounting seat 111, and the third seal 14 is mounted in the seal groove 1112. After the mounting seat 111 is mounted on the feed port 21, an outer side of the third seal 14 abuts against an interior of the feed port 21, such that the sealing after the mounting seat 111 is connected to the feed port 21 may be ensured, and the anesthetic in the tank 22 is prevented from volatilizing to outside through a gap between the mounting seat 111 and the feed port 21.

In an alternative embodiment, the mounting assembly 11 further includes a fixing seat 113, and the fixing seat 113 fixes the liquid injection seat 112 and the mounting seat 111 in the feed port 21 after the liquid injection seat 112 is mounted in the liquid injection seat mounting recess 1111*c*.

In an alternative embodiment, a distance between the end of the valve core assembly 13 facing the tank 22 and the tank 22 is equal to a preset distance. The preset distance may be any natural number greater than or equal to zero so as to ensure that there is a certain distance between the opening at the end of the valve core assembly 13 that extends into the tank 22 and a top end of the tank 22 close to the feed port 21, and thus when the anesthetic bottle is pulled out from the liquid injection seat 112, the anesthetic may flow into the tank 22 along the opening at the end of the liquid inlet channel 131 that extends into the tank 22.

Figure 14:
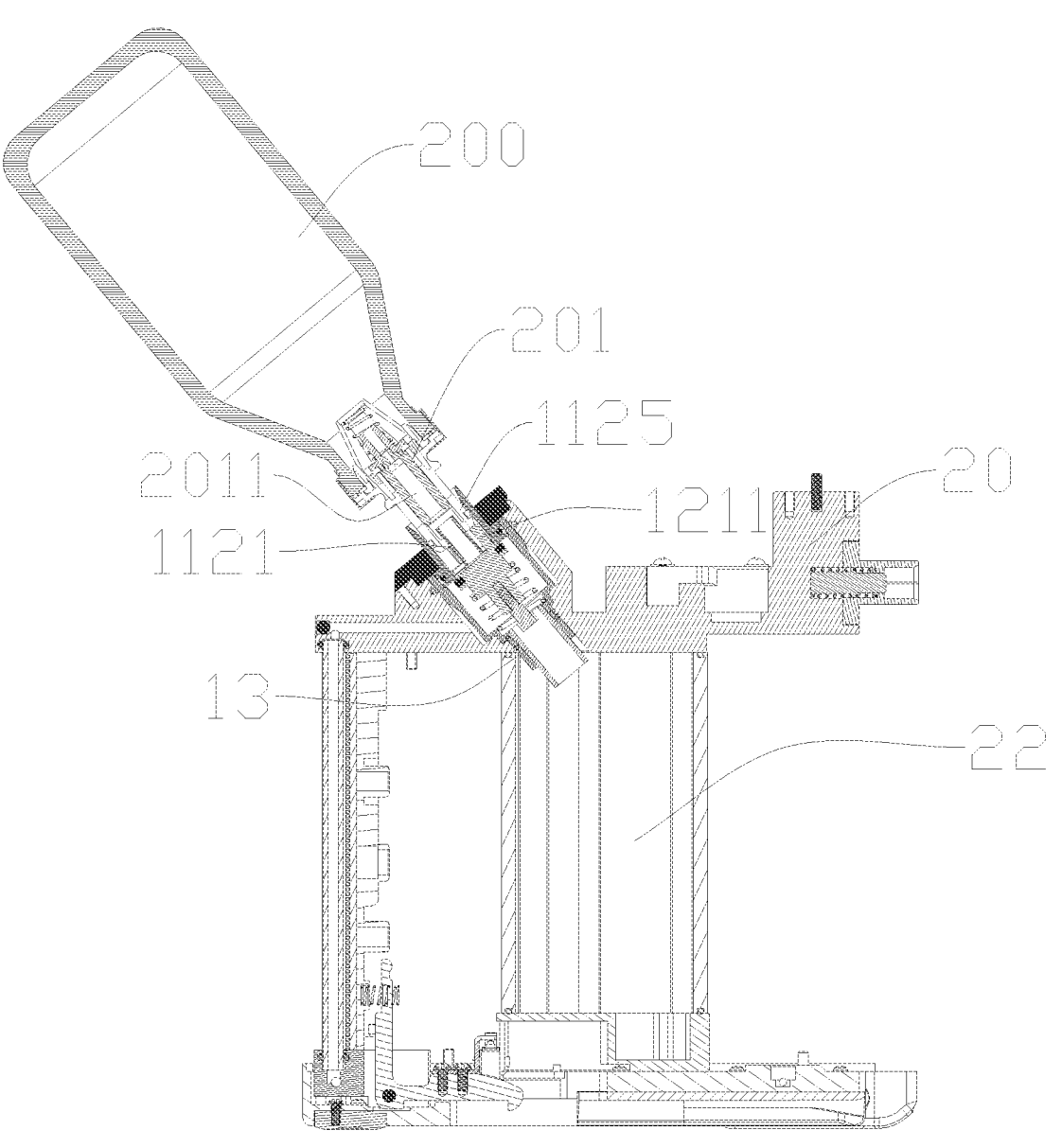
FIG. 14 is a schematic diagram of the perfusion device of FIG. 1 at the beginning of anesthetic feeding.
Figure 15:
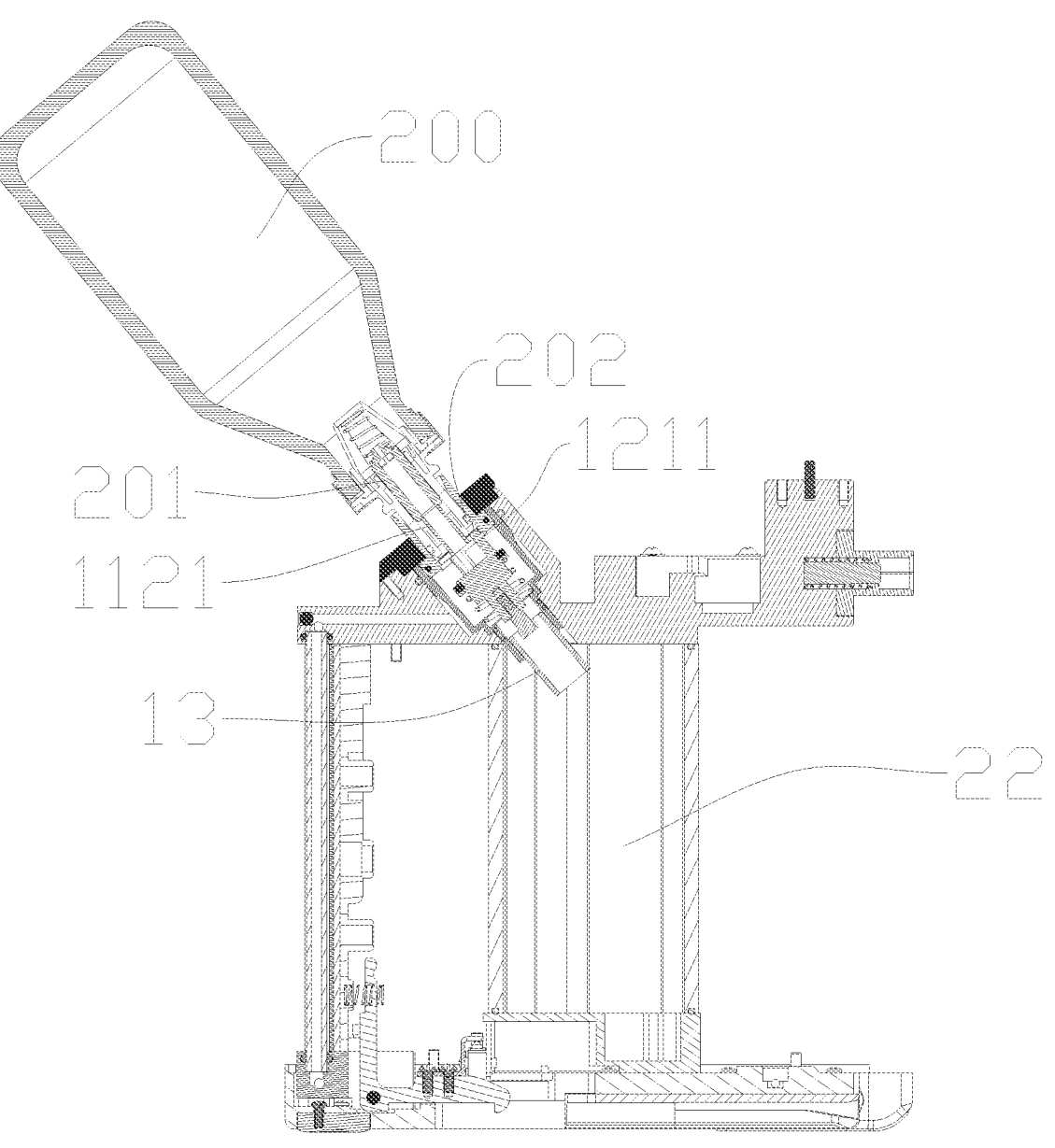
FIG. 15 is a schematic diagram of the perfusion device of FIG. 1 during the anesthetic feeding.
Figure 16:
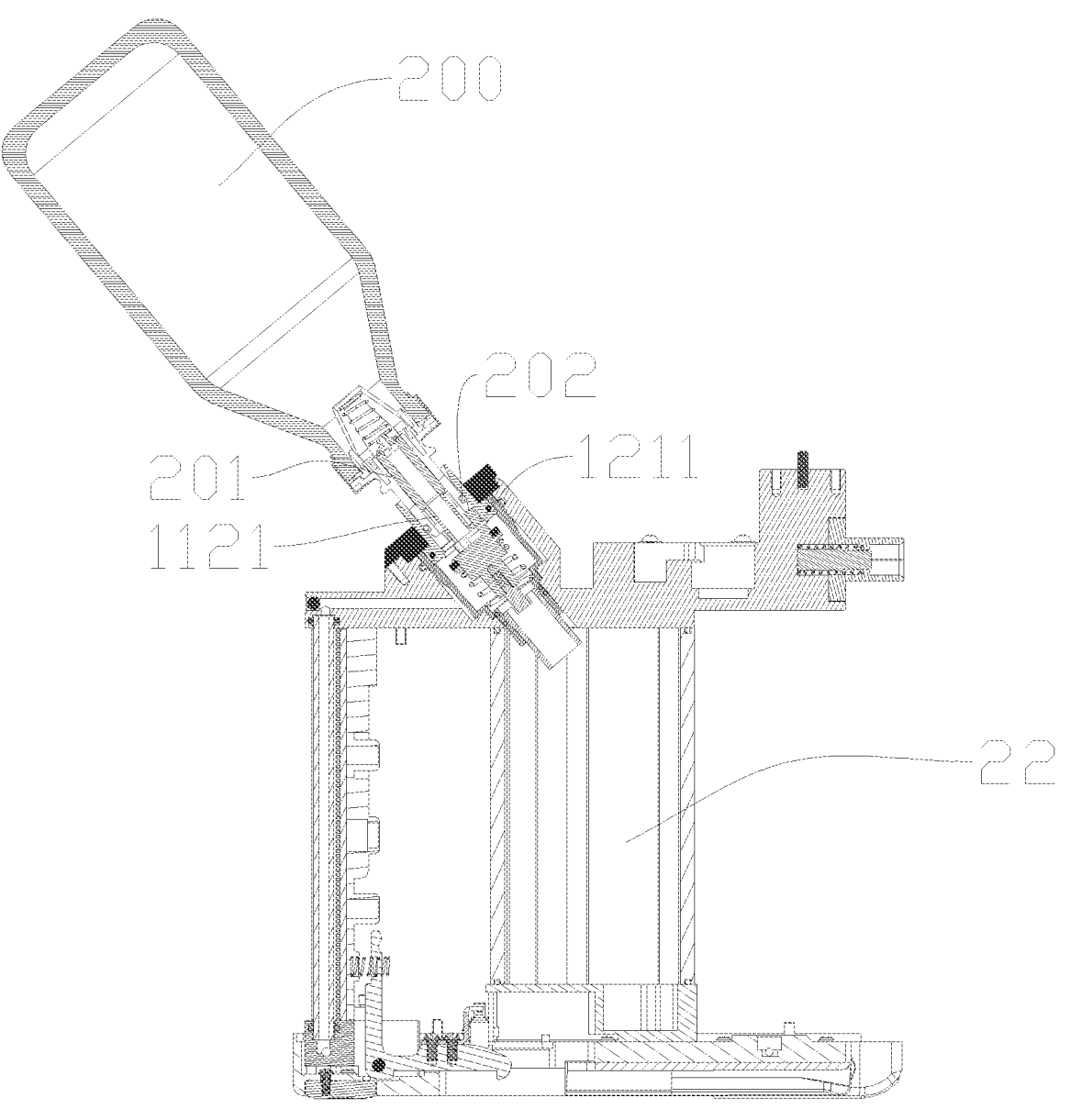
FIG. 16 is a schematic diagram of the perfusion device of FIG. 1 with an anesthetic bottle pulled out.

With the above technical solution, as shown in FIGS. 14 to 16, when the anesthetic bottle 200 is inserted into the liquid injection seat, the sealing device 201 in the anesthetic bottle 200 is ejected by the ejection portion 1121 on the liquid injection seat such that the sealing device 201 moves toward the interior of the anesthetic bottle 200. The anesthetic outlet 2011 on the sealing device 201 corresponds to the liquid inlet hole in the position, such that the anesthetic in the anesthetic bottle 200 can enter the tank 22 through the liquid inlet hole.

When the anesthetic bottle 200 continues moving toward the tank 22, the anesthetic bottle 200 comes into contact with the extension 1211 and drives the extension 1211 to move toward the tank 22. Since the valve core assembly 13 is connected to the ejector rod assembly, the extension 1211 drives the valve core assembly 13 to move toward the tank 22 during the movement, such that the sealing between the ejector rod assembly and the liquid injection seat may be released and the valve core assembly 13 may also be driven to extend into the tank 22.

During the anesthetic feeding, the anesthetic in the anesthetic bottle 200 enters the tank 22 through the hollow structure and the liquid inlet channel, and when the anesthetic in the tank 22 covers the opening of the valve core assembly 13 that extends into the tank 22, the exhaust passage between the tank 22 and the anesthetic bottle 200 is cut off, and therefore, the anesthetic bottle 200 automatically stops feeding the anesthetic into the tank 22, which prevents the overflow and residual anesthetic during the anesthetic feeding and ensures the health of the anesthetic feeding personnel.

When the anesthetic bottle 200 is pulled out from the liquid injection seat, the ejection portion 1121 stops driving the sealing device 201, such that the sealing device 201 returns to its original position, thus preventing the anesthetic from flowing out of the anesthetic bottle 200. Meanwhile, the ejector rod drives the valve core assembly 13 to returns to its original position under the action of the elastic member, such that the ejector rod assembly can form a sealed structure with the mounting assembly again, preventing volatilization of the anesthetic in the tank 22 to outside. When the anesthetic bottle 200 is pulled out from the liquid injection seat, the opening of the valve core assembly 13 that extends into the tank 22 is opened again to re-open the exhaust passage between the tank 22 and the anesthetic bottle 200, such that the anesthetic remaining in the liquid inlet channel can re-enter the tank 22. Therefore, when the anesthetic bottle 200 is pulled out, there is no liquid remaining in the liquid inlet channel.

It should be noted that when the anesthetic bottle 200 is inserted into the liquid injection seat, the seal 202 in the anesthetic bottle 200 firstly provides the sealing effect with the liquid injection seat, and then the sealing device 201 is ejected by the ejection portion 1121 and the sealing between the ejector rod assembly and the liquid injection seat is released, preventing volatilization of the anesthetic in the anesthetic bottle 200 to outside during the anesthetic feeding.

Figure 17:
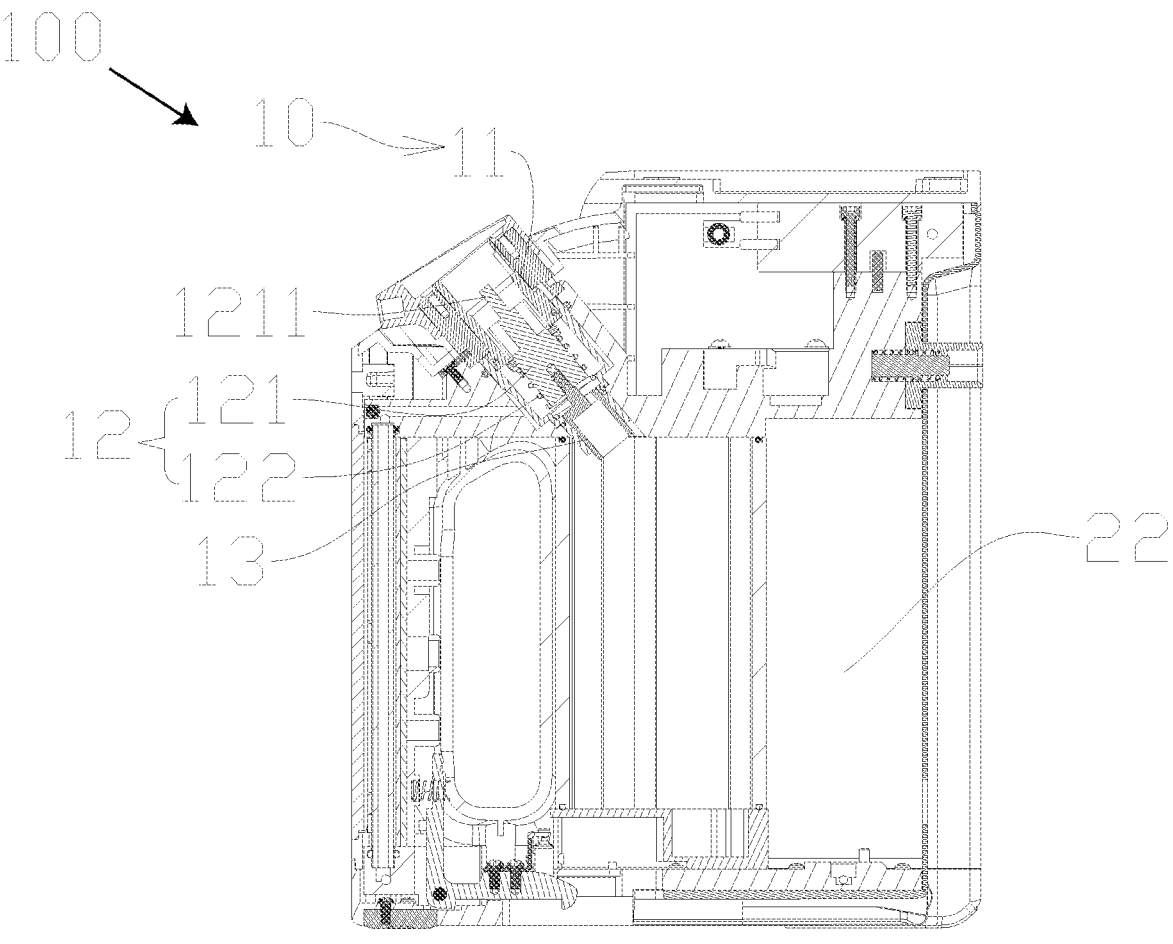
FIG. 17 is a partial cross-sectional view of an anesthetic vaporizer according to another embodiment of the disclosure.
Figure 18:
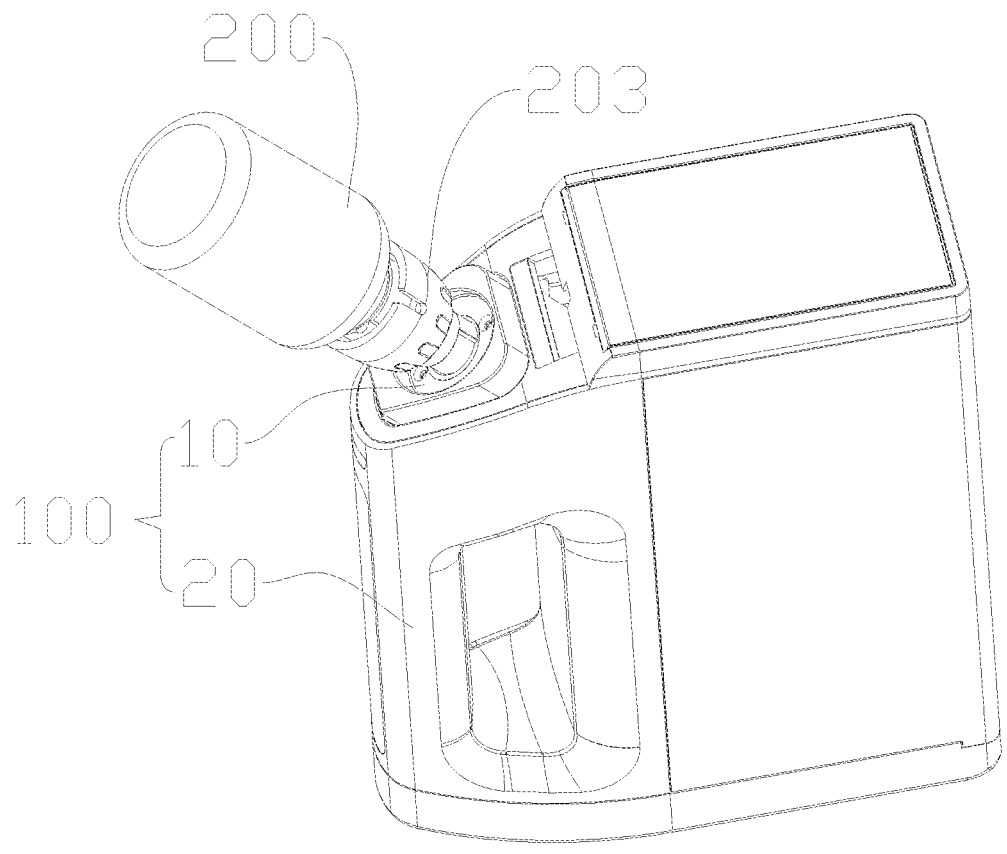
FIG. 18 is a schematic diagram showing that the anesthetic bottle is inserted into the perfusion device of FIG. 17.
Figure 19:
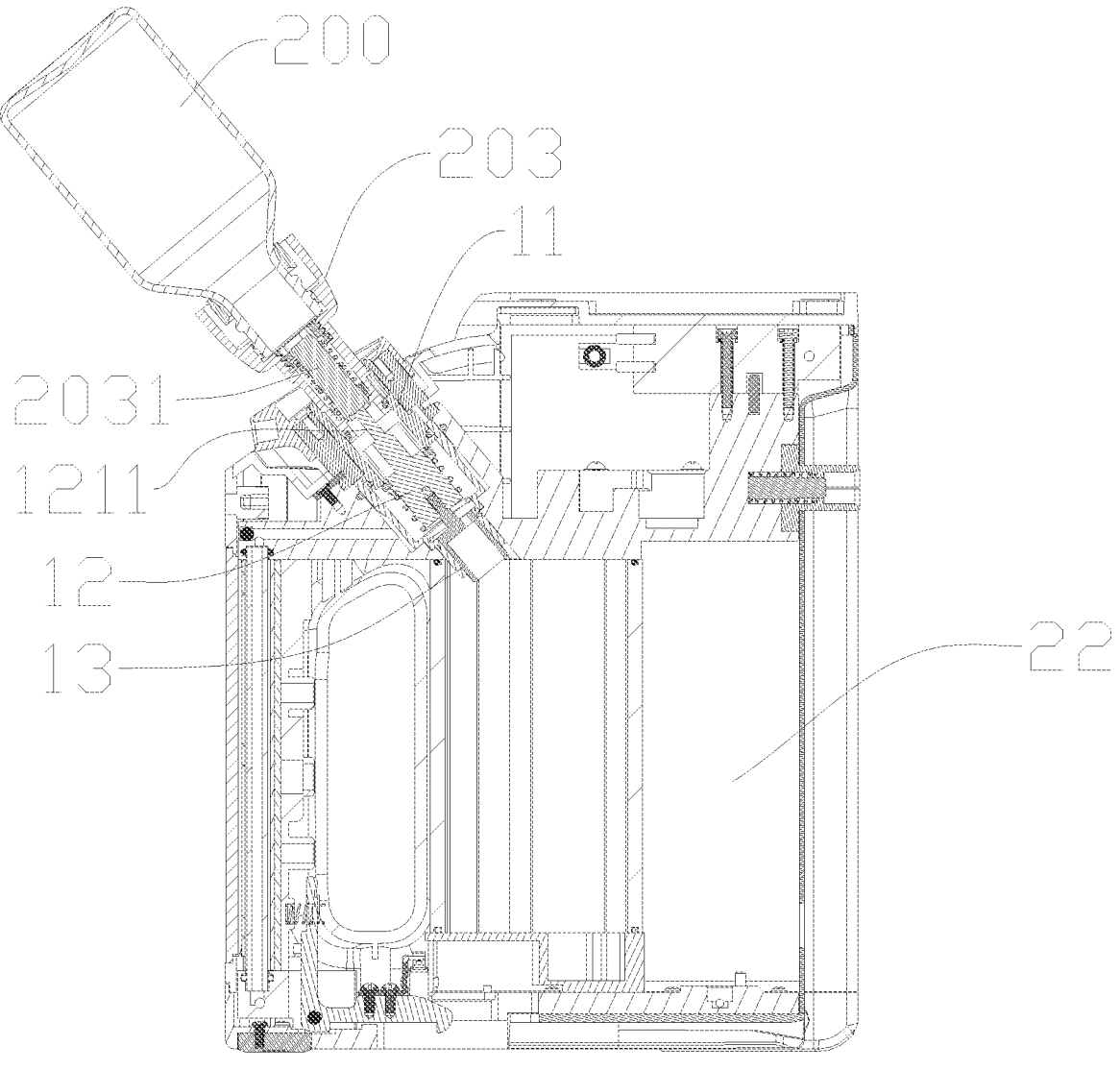
FIG. 19 is a schematic diagram of the perfusion device of FIG. 17 during the anesthetic feeding.

In an alternative embodiment, as shown in FIGS. 16 to 18, the ejection portion and the extension 1211 may be provided as one piece, that is to say, the liquid injection seat is hollow, and the extension 1211 is disposed in the middle of the ejector rod 121. When the anesthetic bottle 200 is inserted into the liquid injection seat, the extension 1211 may eject the sealing device in the anesthetic bottle 200, and meanwhile, the sealing between the ejector rod 121 and the liquid injection seat may be released by a reaction force of the sealing device, such that the anesthetic in the anesthetic bottle 200 can enter the tank 22 through the hollow structure and the liquid inlet channel.

In addition, the anesthetic bottle 200 may feed anesthetic into the tank 22 by means of a feed adapter 203, where a sealing assembly 2031 of the feed adapter 203 may be ejected by the extension 1211, such that the anesthetic in the anesthetic bottle 200 can flow into the hollow structure and the liquid inlet channel by means of the feed adapter 203 and then enter the tank 22.

As shown in FIGS. 1 to 18, according to a second aspect of the disclosure, the disclosure further provides an anesthetic machine, including a main body and the anesthetic vaporizer 100 described above, where the main body of the anesthetic machine is provided with a vaporizer connection seat and a gas supply and delivery system, and the anesthetic vaporizer 100 is mounted on the vaporizer connection seat. In this embodiment, the gas supply and delivery system is connected to the anesthetic vaporizer 100 such that the anesthetic vaporizer 100 can provide respiratory support to the patient through a breathing circuit, thus anesthetizing the patient.

With the above technical solution, it is not only possible to avoid the overflow and residuals of the anesthetic during anesthetic feeding on the main body of the anesthetic machine, but also the health of the anesthetic feeding personnel is ensured. In addition, the respiratory support may also be provided to the patient, and the patient may be then anesthetized for corresponding surgical treatment.

As shown in FIGS. 1 to 18, according to a third aspect of the disclosure, the disclosure further provides a perfusion device for use in an anesthetic vaporizer, where the perfusion device 10 includes the mounting assembly 11, the ejector rod assembly 12 and the valve core assembly 13, and the anesthetic vaporizer 100 has the feed port 21 thereon. In this embodiment, the mounting assembly 11 includes a mounting seat 111 mountable on the feed port 21, the mounting seat 111 having a hollow structure 1111 with openings at its two ends, where the ejector rod assembly 12 may be movably mounted on an opening at the end of the hollow structure 1111 away from the tank 22, and the valve core assembly 13 may be movably mounted on an opening at the other end of the hollow structure 1111, and the valve core assembly 13 is connected to the ejector rod assembly 12, such that the ejector rod assembly 12 can drive the valve core assembly 13 to move in an axial direction of the feed port 21.

In the description of the disclosure, it should be noted that unless explicitly specified and defined otherwise, the terms "mounting", "connecting" and "connection" should be understood in a broad sense, for example, they may refer to a fixed connection, a detachable connection, or an integrated connection, may refer to a mechanical connection or an electrical connection, may refer to a direct connection or an indirect connection via an intermediate medium, and may be internal communication between two elements or an interaction relationship between the two elements. For those of ordinary skill in the art, specific meanings of the foregoing terms in the disclosure may be understood based on specific situations.

In this application, unless expressly stated or limited otherwise, the expression a first feature being "above" or "under" a second feature may include direct contact between the first feature and the second feature, or may include that the first and second features are not in direct contact but are in contact via a further feature therebetween. Furthermore, the expression the first feature being "over", "above" and "on top of" the second feature may be the case that the first feature is directly above or obliquely above the second feature, or only means that the level of the first feature is higher than that of the second feature. The expression the first feature being "underneath", "below" and "beneath" the second feature may be the case that the first feature is directly below or obliquely below the second feature, or only means that the level of the first feature is less than that of the second feature.

This description above provides many different embodiments or examples that are used to implement different structures of the disclosure. In order to simplify the description of the disclosure, the components and arrangements of specific examples are described above. Of course, They are merely examples and are not intended to limit the disclosure. Furthermore, this disclosure may repeat reference numbers and/or reference letters in different examples, such repetition being for purposes of simplicity and clarity and not in itself indicative of a relationship between various embodiments and/or arrangements discussed. In addition, this disclosure provides examples of various specific processes and materials herein, but those of ordinary skill in the art may recognize the application of other processes and/or the use of other materials.

In the description, the explanation with reference to the terms such as "an embodiment", "some embodiments", "exemplary embodiments", "an example", "specific examples", or "some examples" means that specific features, structures, materials, or characteristics described with respect to the embodiment(s) or example(s) are included in at least one embodiment or example of the disclosure. In the description, the illustrative descriptions of the above-mentioned terms don't necessarily refer to the same embodiments or examples. Moreover, the specific features, structures, materials, or characteristics described herein may be combined in any one or more embodiments or examples in a suitable manner.

Although the embodiments of the disclosure have been shown and described, it will be appreciated by those of ordinary skill in the art that: various changes, modifications, substitutions and variations can be made to these embodiments without departing from the principles and spirit of the disclosure, and the scope of the disclosure is defined by the claims and their equivalents.

What is claimed is:

1. An anesthetic vaporizer, comprising:
a vaporizer body provided with a feed port and a tank, the tank communicating with an outside via the feed port; and
a perfusion device comprising a mounting assembly, an ejector rod assembly and a valve core assembly, the valve core assembly provided with a liquid inlet channel, the mounting assembly comprising a mounting seat mounted on the feed port, the mounting seat comprising a hollow structure having openings at two opposite ends of the hollow structure, the valve core assembly being movably mounted on one of the openings at one of the two opposite ends of the hollow structure facing the tank, the ejector rod assembly being movably mounted on another one of the openings at another one of the two opposite ends of the hollow structure and forming a sealed structure with the mounting assembly, the ejector rod assembly being configured to drive the valve core assembly to move toward the tank under an external force, and the liquid inlet channel communicating with the hollow structure,
wherein the mounting assembly further comprises a liquid injection seat configured to receive and engage a mouth of an anesthetic bottle, and the external force is applied to the ejector rod assembly upon engagement of the mouth of the anesthetic bottle with the liquid injection seat.

2. The anesthetic vaporizer of claim 1, wherein the hollow structure comprises an inlet section and an outlet section, and a diameter of the outlet section is smaller than a diameter of the inlet section; the ejector rod assembly is mounted in the inlet section, and the valve core assembly is mounted in the outlet section.

3. The anesthetic vaporizer of claim 2, wherein the ejector rod assembly comprises an ejector rod and an elastic member; one end of the elastic member abuts against the ejector rod, and another end of the elastic member abuts against an end of the inlet section close to the outlet section.

4. The anesthetic vaporizer of claim 3, wherein an end of the ejector rod facing the valve core assembly is provided with a connection end; a diameter of the connection end is smaller than the diameter of the outlet section, and the valve core assembly is connected to the connection end.

5. The anesthetic vaporizer of claim 4, wherein the valve core assembly is provided with a connection portion, and the valve core assembly is connected to the connection end by way of the connection portion.

6. The anesthetic vaporizer of claim 5, wherein at least one valve core through hole, which communicates with the liquid inlet channel, is provided between the connection portion and the valve core assembly.

7. The anesthetic vaporizer of claim 3, wherein the inlet section is provided with a liquid injection seat mounting recess, and the liquid injection seat is mounted on the liquid injection seat mounting recess, so as to constrain the ejector rod assembly within the hollow structure.

8. The anesthetic vaporizer of claim 7, wherein the liquid injection seat is provided with an ejection portion, and when the mouth of the anesthetic bottle is connected to the liquid injection seat, a sealing part mounted in the mouth of the anesthetic bottle is ejected by the ejection portion.

9. The anesthetic vaporizer of claim 8, wherein the ejection portion is provided with a liquid inlet hole running through two axial ends of the ejection portion, and the liquid inlet hole corresponds in position to the mouth of the anesthetic bottle connected to the liquid injection seat.

10. The anesthetic vaporizer of claim 8, wherein at least one penetrating hole is provided between the ejection portion and the liquid injection seat, and the ejector rod is provided with an extension which penetrates the at least one penetrating hole; when the anesthetic bottle is placed on the liquid injection seat, the anesthetic bottle is capable of driving the ejector rod away from the liquid injection seat by way of the extension.

11. The anesthetic vaporizer of claim 10, wherein a length of the extension extending from the liquid injection seat is less than a length of the ejection portion extending from the liquid injection seat.

12. The anesthetic vaporizer of claim 7, wherein the ejector rod assembly further comprises a first seal disposed between the ejector rod and the liquid injection seat.

13. The anesthetic vaporizer of claim 7, wherein a seal is provided between the liquid injection seat and the mounting seat, and the liquid injection seat is provided with a seal mounting groove in which the seal is mounted.

14. The anesthetic vaporizer of claim 1, wherein a seal is provided between the mounting seat and the feed port, a seal groove is provided along a periphery of the mounting seat, and the seal is mounted in the seal groove.

15. The anesthetic vaporizer of claim 1, wherein a distance between an end of the valve core assembly facing the tank and the tank is equal to a preset distance.

16. An anesthetic machine comprising an anesthetic vaporizer, the anesthetic vaporizer comprising:

a vaporizer body provided with a feed port and a tank, and the tank communicating with an outside via the feed port;

a perfusion device comprising a mounting assembly, an ejector rod assembly and a valve core assembly, the valve core assembly provided with a liquid inlet channel, the mounting assembly comprising a mounting seat mounted on the feed port, the mounting seat comprising a hollow structure having openings at two opposite ends of the hollow structure, the valve core assembly being movably mounted on one of the openings at one of the two opposite ends of the hollow structure facing the tank, the ejector rod assembly being movably mounted on another one of the openings at another one of the two opposite ends of the hollow structure and forming a sealed structure with the mounting assembly, the ejector rod assembly being configured to drive the valve core assembly to move toward the tank under an external force, and the liquid inlet channel communicating with the hollow structure, wherein the mounting assembly further comprises a liquid injection seat configured to receive and engage a mouth of an anesthetic bottle, and the external force is applied to the ejector rod assembly upon engagement of the mouth of the anesthetic bottle with the liquid injection seat.

17. A perfusion device for use in an anesthetic vaporizer with a feed port and a tank, comprising:

a mounting assembly comprising a mounting seat mounted on the feed port, the mounting seat comprising a hollow structure having openings at two opposite ends of the hollow structure;

a valve core assembly provided with a liquid inlet channel and movably mounted on one of the openings at one of the two opposite ends of the hollow structure facing the tank; and an ejector rod assembly movably mounted on another one of the openings at another one of the two opposite ends of the hollow structure and forming a sealed structure with the mounting assembly, the ejector rod assembly driving the valve core assembly to move toward the tank under an external force, and the liquid inlet channel communicating with the hollow structure, wherein the mounting assembly further comprises a liquid injection seat configured to receive and engage a mouth of an anesthetic bottle, and the external force is applied to the ejector rod assembly upon engagement of the mouth of the anesthetic bottle with the liquid injection seat.

\* \* \* \* \*